US006676978B1

(12) United States Patent
Nair

(10) Patent No.: US 6,676,978 B1
(45) Date of Patent: Jan. 13, 2004

(54) METHOD AND COMPOSITIONS FOR PRODUCING BERRY DERIVED PRODUCTS

(75) Inventor: Muraleedharan G. Nair, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 09/678,587

(22) Filed: Oct. 3, 2000

Related U.S. Application Data

(60) Division of application No. 09/383,324, filed on Aug. 26, 1999, which is a continuation-in-part of application No. 09/317,310, filed on May 24, 1999, now Pat. No. 6,423,365
(60) Provisional application No. 60/120,178, filed on Feb. 16, 1999.

(51) Int. Cl.$^7$ ......................... A61K 35/78; A61K 31/70; A61K 31/215; A61K 31/235; A01N 43/04
(52) U.S. Cl. ..................... 424/735; 424/777; 424/725; 514/533; 514/529; 514/28; 514/27
(58) Field of Search ............................. 426/450, 102, 426/103, 540, 639, 655; 424/195.1, 725, 735, 777; 514/533, 529, 27, 28

(56) References Cited

U.S. PATENT DOCUMENTS

| | | | |
|---|---|---|---|
| 4,115,595 A | * 9/1978 | Jordan ........................ | 426/250 |
| 4,297,220 A | 10/1981 | Meitzner et al. | |
| 4,481,226 A | * 11/1984 | Crosby et al. .............. | 426/540 |
| 5,266,685 A | 11/1993 | Garbutt | |
| 5,503,867 A | 4/1996 | Pleva | |
| 5,665,783 A | 9/1997 | Katzakian et al. | |
| 5,817,354 A | 10/1998 | Mozaffar | |

OTHER PUBLICATIONS

Volpe, T. Cranberry Juice Concentrate as a Red Food Coloring; Food Product Development, 10(9), pp. 13–14, 1976.*
McLellan et al. Application of Anthocyanins as Colorants for Maraschino–Type Cherries; Journal of Food Science, vol. 44, No. 2, pp. 483–487, 1979.*
Timberlake et al. Anthocyanins; Color Augmentation with Catechin; Journal Sci. Food Agriculture, vol. 28, pp. 539–544, 1977.*
Markakis, P. Anthocyanins and Their Solubility in Foods; CRC Critical Review in Food Technology, vol. 4, no. 4, pp. 437–456, 1974.*
Chandra et al. Isolation and Stabilization of Anthocyanins From Tart Cherries (*Pruns cerasus* L.), 1993, J. Agric. Food Chem., 41, pp. 1062–1065.
Kinsella et al., Food Tech. 85–89 (1993).
Tsuda, T., et al., J. Agric. Food Chem. 42:2407–2410 (1994).
Halliwell, B. and J.M.C. Gutteridge, Free radicals in biology and medicine. Oxford Univ. Press, New York 416–494 (1989).
Osawa, T., et al., Role of dietary antioxidants in protection against oxidative damage. In anti–mutagenesis and anticarcinogenesis Mechanisms; Kuroda, Y.: Shankel, D.M., Waters, M.D., Eds. Plenum Publishing. New York 139–153 (1990).
Li, K. C., et al., J. Am. Chem. Soc. 78:979–980 (1956).
Harborne, J. B., et al., Pytochemistry 3:453–463 (1964).
Dekazos, E.D., J. Food Sci. 35:237–241 (1970).
Chandra, A., et al., J. Agric. Food Chem. 40:967–969 (1992).
Shrikhande, A.J. and F.J. Francis, J. Food Sci. 38:649–651 (1973).
Chandra, A., et al., J. Agric. Food Chem. 41:1062–1065 (1993).
Gomaa et al., IFT Abstracts No. 68E–7 (1996).
Wang, H., et al., J. Agric. Food Chem. 45:2556–2560 (1997).
Arora, A. and G. M. Strasburg, J. Amer. Oil Chem. Soc. 74:1031–1040 (1997).
MacDonald, R.C., et al., Biochim. Biophys. Acta 1061:297–303 (1991).
Wang, et al., J. Nat. Products 62:294–296 (1999).
Wang, et al., J. of Ag. and Food Chemistry 47:840–844 (1999).
Wang, et al., J. of Nat. Products, 62:86–88 (1999).

* cited by examiner

*Primary Examiner*—Patricia Patten
(74) *Attorney, Agent, or Firm*—Ian C. McLeod

(57) ABSTRACT

A method for isolating a mixture of anthocyanins, bioflavonoids and phenolics from an edible berry using adsorbent resins which are regenerable for reuse is described. The mixture with a consumable carrier is particularly useful in foods and as a dietary supplement or nutraceutical product.

8 Claims, 6 Drawing Sheets

| | $R_1$ | $R_2$ |
|---|---|---|
| Anthocyanin 1 (cyanidin-3-glucosylrutinoside) |  |  |
| Anthocyanin 2 (cyanidin-3-rutinoside) | H |  |
| Anthocyanin 3 (cyanidin-3-glucoside) | H | H |

| Compound | $R_1$ | $R_2$ | $R_3$ | $R_4$ | $R_5$ | $R_6$ | $R_7$ |
|---|---|---|---|---|---|---|---|
| Quercetin | OH | OH | OH | OH | H | OH | H |
| Kaempferol | OH | H | OH | OH | H | OH | H |
| Luteolin | OH | OH | H | OH | H | OH | H |
| Quercetrin | OH | OH | rhamnose | OH | H | OH | H |
| Kaempferol 3-rutinoside | OH | H | rutinose | OH | H | OH | H |
| 3'-methoxy kaempferol 3-rutinoside | OH | OMe | rutinose | OH | H | OH | H |
| 5,8,4'-trihydroxyl-6,7-dimethoxyflavone | OH | H | H | OH | OMe | OH | OMe |

| Compound | $R_1$ | $R_2$ | $R_3$ |
|---|---|---|---|
| Genistein | OH | OH | OH |
| Genistin | OH | OH | glucose |
| Biochanin A | OMe | OH | OH |
| Daidzein | OH | H | OH |
| Formononetin | OMe | H | OH |

METHOD AND COMPOSITIONS FOR PRODUCING BERRY DERIVED PRODUCTS

CROSS REFERENCE TO RELATED APPLICATIONS

This application is a Divisional Application of U.S. application Ser. No. 09/383,324, filed Aug. 26, 1999, which is a Continuation-in-part of U.S. application Ser. No. 09/317,310, filed May 24, 1999 now U.S. Pat. No. 6,423,365 Jul. 23, 2002, and this application also claim s priority to U.S. Provisional Application Serial No. 60/120,178, filed Feb. 16, 1999.

STATEMENT REGARDING FEDERALLY SPONSORED RESEARCH OR DEVELOPMENT

None

BACKGROUND OF THE INVENTION (1) Summary of the Invention

The present invention relates to a method of preparation of edible berry derived compositions, particularly cherry, and to a method of use of the compositions derived from the berries as phytoceutical/nutraceutcal dietary supplements or as an additive to foods. In particular, the present invention provides a natural berry composition, particularly cherry, containing a mixture of anthocyanins, bioflavonoids and phenolics for use as dietary supplements or as a food additive.

(2) Description of Related Art

Many plant-derived compounds may also impart important positive pharmacological or "nutraceutical" traits to foods by way of their abilities to serve as cellular antioxidants by maintaining low levels of reactive oxygen intermediates, as anti-inflammatory agents by inhibiting prostaglandin synthesis, or as inhibitors of enzymes involved in cell proliferation. These activities may be important in ameliorating chronic diseases including cancer, arthritis, and cardiovascular disease (Kinsella et al., Food Tech. 85–89 (1993). Thus, with natural products, the dietary supplement/food industry and nutraceutical companies has the opportunity to employ compounds which can not only enhance food stability as effectively as synthetic antioxidants, but can also offer significant health benefits to the consumer.

Colorants like anthocyanins have been regarded as the index of quality in tart cherries. Most importantly, recent results showed that anthocyanins such as cyanidin-3-glucoside have strong antioxidant activities (Tsuda, T., et al, J. Agric. Food Chem. 42:2407–2410 (1994)). The addition of antioxidants is one of the popular methods to increase the shelf life of food products which is thought to be associated with lipid peroxidation. Natural antioxidants may play an important role in the prevention of carcinogenesis. Dietary antioxidants may be effective against the peroxidative damage in living systems (Halliwell, B. and J. M. C. Gutteridge, Free radicals in biology and medicine. Oxford University Press, New York 416–494 (1989); Osawa, T., et al, Role of dietary antioxidants in protection against oxidative damage. In antimutagenesis and anticarcinogenesis Mechanisms; Kuroda, Y.; Shankel, D. M., Waters, M. D., Eds.; Plenum Publishing. New York 139–153 (1990)).

Early studies have showed that MONTMORENCY cherry contains the anthocyanins cyanidin-3-gentiobioside and cyanidin-3-rutinoside (Li, K. C., et al., J. Am. Chem. Soc. 78:979–980 (1956)). Cyanidin-3-glucosylrutinoside was also found in six out of the seven sour cherry varieties (Harborne, J. B., et al., Phytochemistry 3:453–463 (1964)). Dekazos (Dekazos, E. D., J. Food Sci. 35:237–241 (1970)) reported anthocyanin pigments in MONTMORENCY cherry as peonidin-3-rutinoside, peonidin and cyanidin along with cyanidin-3-sophoroside, cyanidin-3-rutinoside and cyanidin-3-glucoside. However, cyanidin-3-glucosylrutinoside as well as cyanidin-3-glucoside, cyanidin-3-sophoroside and cyanidin-3-rutinoside were identified as main pigments in sour cherries. Using HPLC retention values, Chandra et al (Chandra, A., et al., J. Agric. Food Chem. 40:967–969 (1992)) reported that cyanidin-3-sophoroside and cyanidin-3-glucoside were the major and minor anthocyanins, respectively, in Michigan grown MONTMORENCY cherry. Similarly, cyanidin-3-xylosylrutinoside was detected as a minor pigment in MONTMORENCY cherry (Shrikhande, A. J. and F. J. Francis, J. Food Sci. 38:649–651 (1973)).

In the prior art, production of pure anthocyanins (compounds 1–3 of FIG. 1) from BALATON and MONTMORENCY cherry juices was carried out first by adsorbing the pigment on an AMBERLITE XAD-2 (Sigma Chemicals) column (Chandra, A., et al., J. Agric. Food Chem. 41:1062–1065 (1993)). The column was washed with water until the eluant gave a pH of approximately 7.0. The adsorbed pigments along with other phenolics were eluted with MeOH. The resulting crude anthocyanins were fractionated and purified by C-18 MPLC and HPLC, respectively, to afford pure anthocyanins for spectral studies. Purification of 500 mg crude MONTMORENCY anthocyanins from AMBERLITE XAD-2 yielded 60 mg of pure anthocyanins 1–3 compared to 391.43 mg from BALATON. This research indicated that crude anthocyanins from MONTMORENCY obtained from the XAD-2 contained a high percentage of other organic compounds. The AMBERLITE XAD-2 did not allow recycling of the resin. There was no attempt to use the crude mixture of phenolics and anthocyanins for any purpose. U.S. Pat. No. , 5,266,685 to Garbutt, U.S. Pat. No. 5,665,783 to Katzakian et al and U.S. Pat. No. 5,817,354 to Mozaffar describe various adsorbent resins and their use for unrelated products. These patents are only illustrative of the general state of the art in the use of adsorbent resins.

U.S. Pat. No. 5,503,867 to Pleva describes the use of whole ground cherries and oat bran in ground meat. The amount of cherries used was 10 to 15% by weight and the oat bran is believed to be added to compensate for the juice in the cherries. In any event, the cherries definitely contribute a flavor to the meat and the palatability of the product is not universally accepted.

Recent studies on stabilization of low-fat ground beef with cherry tissue suggest that this plant source contains potent antioxidants which not only suppress lipid peroxidation, but also inhibit formation of heterocyclic aromatic amines and cholesterol oxidation products during frying (Gomaa et al., IFT Abstracts No. 68E-7 (1996). The hypothesis used to explain these observations was that polyphenols, such as flavonoids, anthocyanins and anthocyanidins, frequently found in the vacuoles of higher plants such as the cherries were responsible for this antioxidant effect.

There is a need for natural edible berry derived compositions for use, particularly as dietary supplements/nutraceutical or food additives.

SUMMARY OF THE INVENTION

The present invention relates to a method for producing a mixture comprising anthocyanins, bioflavonoids and phenolics from an edible berry as a composition which comprises:

(a) providing an aqueous solution containing the anthocyanins, bioflavonoids and phenolics from the berry;

(b) removing the anthocyanins, bioflavonoids and phenolics onto a resin surface from the aqueous solution;

(c) eluting the resin surface with a eluant to remove the anthocyanins, bioflavonoids and phenolics from the resin surface; and (d) separating the eluant from the anthocyanins, bioflavonoids and phenolics.

Further, the present invention relates to a method for producing anthocyanins, bioflavonoids and phenolics from an edible berry as a composition which comprises:

(a) providing a first batch of berry, wherein the cherries are fresh or quick frozen and thawed;

(b) disrupting the berry and separating pulp from the juice;

(c) extracting the anthocyanins, bioflavonoids and phenolics from the pulp into an aqueous solution;

(d) removing the anthocyanins, bioflavonoids and phenolics onto adsorbent resin particles from the aqueous solution containing the anthocyanins, bioflavonoids and phenolics separated from the pulp;

(e) washing the resin particles with a lower alkanol to remove the anthocyanins, bioflavonoids and phenolics from the resin particles;

(f) separating the alkanol from the anthocyanins, the bioflavonoids and phenolics; and (g) repeating steps (a) to (e) with the separated alkanol and the resin particles from which the anthocyanins, bioflavonoids and phenolics have been removed with a second batch of the berry.

Further, the present invention relates to a consumable composition which comprises in admixture:

(a) dried mixture of isolated anthocyanins, bioflavonoids and phenolics from an edible berry; and (b) a food grade carrier, wherein the weight ratio of (a) to (b) is between about 0.1 to 100 and 100 to 0.1.

Finally, the present invention relates to a method for feeding a mammal which comprises:

feeding the mammal a consumable composition which comprises in admixture:

(a) dried mixture of isolated anthocyanins, bioflavonoids and phenolics removed from an edible berry; and (b) a food grade carrier wherein the weight ratio of (a) to (b) is between about 0.1 to 100 and 100 to 0.1. It is preferred that the composition contain at least in part dried pulp of the berry.

The term "anthocyanins" means the compounds that impart color in cherries.

The term "bioflavonoids" means the isoflavonoids and flavonoid compounds contained in cherries.

The term "phenolics" refers to compounds with a phenyl group and having one or more hydroxyl groups from cherries.

Some of the edible berries are cranberry, raspberry, strawberry, blueberry, blackberry, elderberry, red grapes, gooseberry, Barbados cherry (acerola cherry) and choke cherry.

OBJECTS

It is therefore an object of the present invention to provide a natural source edible berry composition which can be used in foods or as dietary supplements or nutraceuticals. Further, it is an object of the present invention to provide a method for isolating the composition on a commercial scale. Finally, it is an object of the present invention to provide a natural source composition which is economical to prepare and easy to use. These and other objects will become increasingly apparent by reference to the following description and the drawings.

DESCRIPTION OF PREFERRED EMBODIMENTS

Figure 1:
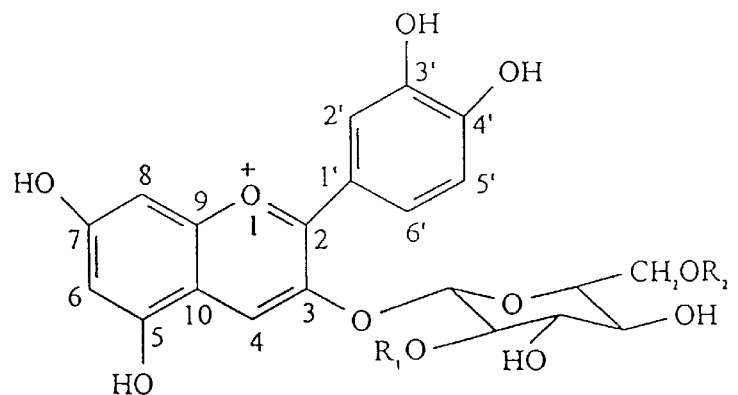
FIG. 1 shows the structure of the isolated anthocyanins (colorants) from BALATON and MONTMORENCY cherries. The aglycone cyanidin has a hydroxyl group at position 3.
Figure 1:
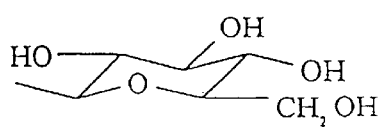
Figure 1:
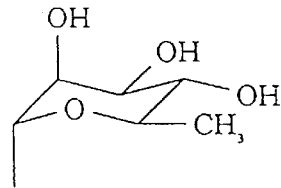
Figure 1:
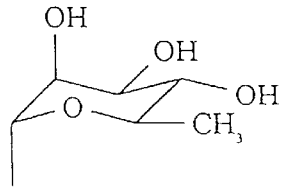

The cherries used in the present invention can be sweet or sour, although the latter are preferred since they contain high levels of malic acid in addition to other organic acids which contributes to the sour taste of tart cherries. The method of the present invention isolates malic acid and other organic acids containing sugars which can be used in foods to provide tartness and flavor. Most preferred are the BALATON and MONTMORENCY cherries.

The isolated mixture of anthocyanins, bioflavonoids and phenolics can be tableted and used as a natural nutraceutical/dietary supplement. In general, the tablets provide a daily dose of the anthocyanins and bioflavonoids of about 1 to 200 mg, preferably a daily dose of 60–100 mg. One hundred (100) cherries provide 60 to 100 mg of anthocyanins. The phenolics (FIG. 4) are provided in an amount of 0.1 to 50 mg as a daily dose. One hundred cherries provide 1–50 mg of phenolics. The amount of the anthocyanins, bioflavonoids and phenolics can be adjusted by isolating the individual compounds and blending them together. It is preferred to use the natural mixture of the anthocyanins, bioflavonoids and phenolics which is isolated by the resin.

The resin has a surface to which the anthocyanins, bioflavonoids and the phenolics are adsorbed. A preferred class of adsorptive resins are polymeric crosslinked resins composed of styrene and divinylbenzene such as, for example, the AMBERLITE series of resins, e.g., AMBERLITE XAD-4 and AMBERLITE XAD-16, which are available commercially from Rohm & Haas Co., Philadelphia, Pa. Other polymeric crosslinked styrene and divinylbenzene adsorptive resins suitable for use according to the invention are XFS-4257, XFS-4022, XUS-40323 and XUS-40322 manufactured by The Dow Chemical Company, Midland, Mich., and the like.

It is preferred to use commercially available, FDA-approved, styrene-divinyl-benzene (SDVB) cross-linked copolymer resin, (e.g., AMBERLITE XAD-16). Thus, in the preferred embodiment, AMBERLITE XAD-16, commercially available from Rohm and Haas Company, and described in U.S. Pat. No. 4,297,220, herein incorporated by reference, is used as the resin. This resin is a non-ionic hydrophobic, cross-linked polystyrene divinyl benzene adsorbent resin. AMBERLITE XAD-16 has a macroreticular structure, with both a continuous polymer phase and a continuous pore phase. In a particularly preferred embodiment, the resin used in the present invention has a particle size ranging from 100–200 microns.

It is contemplated that other adsorbents such as those in the AMBERLITE XAD adsorbent series which contain hydrophobic macroreticular resin beads, with particle sizes in the range of 100–200 microns, will also be effective in the methods of the present invention. Moreover, different variations of the AMBERLITES, such as the AMERCHROM CG series of adsorbents, used with particle sizes in the range of 100–200 microns, may also be suitable for use in the present invention. The AMBERLITE XAD-16 is preferred since it can be re-used many times (over 100 times) However, it is contemplated that for food, the use of governmentally-approved resins in the present invention will be considered important and/or desirable.

Any solvent can be used to remove the adsorbed anthocyanins, bioflavonoids and phenolics. Preferred are lower alkanols containing 1 to 4 carbon atoms and most preferred is ethanol (ethyl alcohol) since it is approved for food use. Typically the ethanol is azeotroped with water; however, absolute ethanol can be used. Water containing malic acid and sugars in the cherries pass through the column. These are collected and can be used in foods as flavors.

The anthocyanins, bioflavonoids and phenolics are preferably isolated from the BALATON and the MONT-MORENCY cherries. The composition of the cherries is in part shown in part by U.S. application Ser. No. 08/799,788 filed Feb. 12, 1997 and in part U.S. application Ser. No. 60/111,945, filed Dec. 11, 1998 which are incorporated by reference herein.

The term "carrier" or "bulking agent" is used to mean a composition which is added to increase the volume of the composition of the purified composition from the cherry. Preferred is dried cherry pulp. These include any edible starch containing material, protein, such as non-fat dry milk. Within this group are flour, sugar, soybean meal, maltodextrin and various condiments, such as salt, pepper, spices and herbs, for instance. The bulking agent is used in an amount between about $10^{-6}$ and $10^6$ parts by weight of the mixture.

The composition is introduced into the food in an amount between about 0.1 and 10 mg/gm of the active ingredients of the food. The amount is preferably selected so as to not affect the taste of the food and to produce the most beneficial result. The food can be high (wet) or low moisture (dry) as is well known to those skilled in the art. When used as a dietary supplement the tablets contain between 0.1 to 1 gram of active ingredient.

Figure 2:
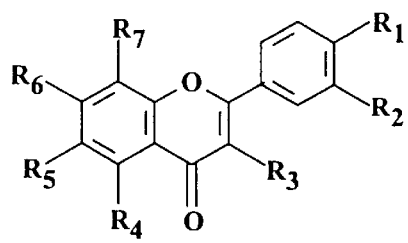
FIGS. 2 and 3 are drawings showing the major bioflavonoids isolated from the cherries, as described in provisional application Serial No. 60/111,945, filed Dec. 11, 1998.
Figure 3:
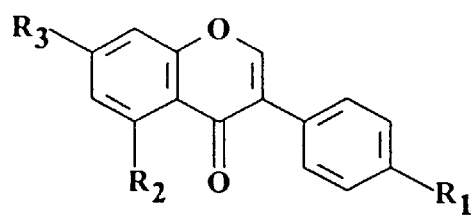

Methods have been developed for extraction and isolation of phytochemicals (Chandra, A., et al., J. Agric. Food Chem. 41:1062 (1992); Wang, H., et al., J. Agric. Food Chem. 45:2556–2560 (1997)) and for rapid screening of antioxidant activity (Arora, A. and G. M. Strasburg, J. Amer. Oil Chem. Soc. 74:1031–1040 (1997)). These methods are being utilized to identify and characterize the antioxidant compounds from BALATON and MONTMORENCY cherries. Juiced cherry tissue was sequentially extracted with hexane, ethyl acetate and methanol. Both methanol and ethyl acetate fractions showed strong antioxidant activity in the screening assay. The ethyl acetate fraction was further purified by silica gel vacuum liquid chromatography to yield four subfractions; the subfraction which showed the strongest antioxidant activity was further separated into seven fractions by preparative reverse phase HPLC. FIGS. 2 and 3 show the bioflavonoids isolated from the BALATON cherries. There are thus numerous analogous or homologous compounds in the tart cherries.

Figure 4:
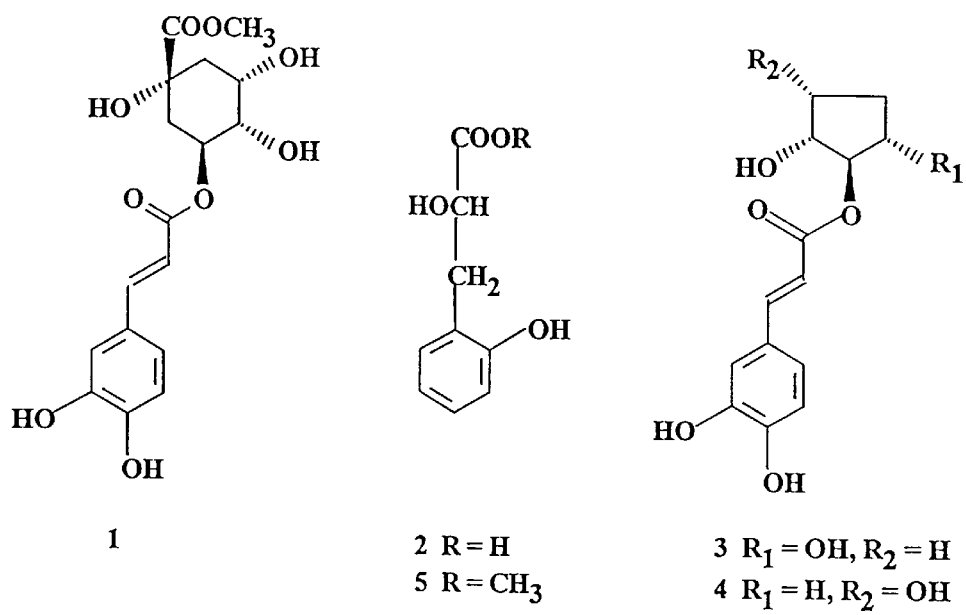
FIG. 4 shows the phenolics isolated from tart cherries.

Two novel phenolic compounds were identified: I) 1-(3'-4'-dihydroxy cinnamoyl)-2,3-dihydroxy cyclopentane, and II) 1-(3'-4'-dihydroxy cinnamoyl)-2,5-dihydroxy cyclopentane. Other compounds isolated from the ethyl acetate extract of cherry fruits and characterized by spectral methods include: 1-(3'-methoxy, 4'-hydroxy cinnamoyl) quinic acid, 2-hydroxy-3-(21-hydroxyphenyl) propanoic acid, methyl 2-hydroxy-3-(2'-hydroxyphenyl) propanoate, D(+)-malic acid, β-sitosterol ad β-sitosterol glucoside. FIG. 4 shows some of the phenolics which were isolated. The anthocyanin components obtained from the juice fraction also have been identified and fully characterized (Chandra, A., et al., J. Agric. Food Chem. 41:1062 (1992); Wang, H., et al., J. Agric. Food Chem. 45:2556–2560 (1997)); the results indicate that these compounds contain potent antioxidant activity.

EXAMPLES 1 and 2

Figure 5:
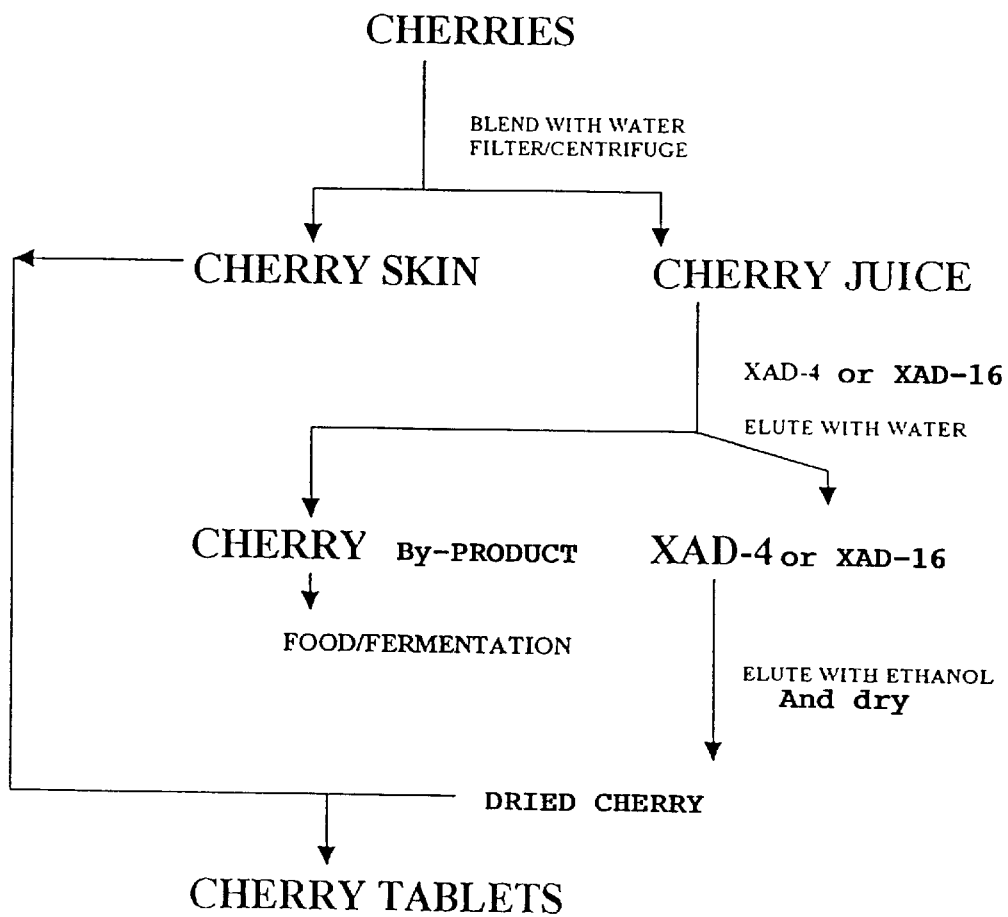
FIG. 5 shows the steps in the method of the present invention as described in Examples 1 and 2.

As shown in FIG. 5, individual quick frozen (IQF) cherries (which had been pitted) were defrosted and blended in an industrial WARING blender. The mixture was centrifuged at 10,000 rpm and the juice was decanted. The residue, pulp, was further pressed with cheese cloth to remove any additional juice.

The pulp was lyophilized at 15° C. The juice was processed on AMBERLITE XAD-16 HP resin to produce cherry sour, anthocyanins, bioflavonoids and phenolics. The XAD-16 resin, 1 kg, was washed with ethanol (1–2 L) and then washed with water (6 L). The XAD-16 resin was allowed to stand in water for 1 hour before loading into a glass column (10 ID×90 cm long) with a cotton plug. The packed column was washed with water (2 L) before loading the juice for separation. 800 mL juice was purified each time. The juice was added onto the surface of the column and allowed to settle with no flow. It was then eluted with water and the first 1 L was discarded. The next 2 L of washing was collected, since it contained the cherry juice which was sour since it contained malic acid and sugars from the cherries. The column was then washed with an additional 4 L of water in the case of BALATON and 5 L for MONTMORENCY cherry juice. Once the cherry juice was collected, the remainder of the washing with water were discarded. The column was then eluted with ethanol (1.3–1.5 L) and collected the red solution containing anthocyanins, bioflavonoids and phenolics (700–800 ml). The column was then run dry and washed with 10 L of water before repeating the process many of times (over 100).

The red alcoholic solution was then evaporated under vacuum a (20 millitorr) to remove ethanol and the aqueous solution, stabilized with 50 ppm ascorbic acid, was lyophilized at 10° C. The red powder was collected and stored.

Example 1 results:

BALATON cherry

| | |
|---|---|
| Weight of IQF cherries | 15.74 kg |
| Weight of dried pulp | 605 g |
| Volume of juice | 12.16 L |
| Weight of anthocyanins, bioflavonoids and phenolics (red powder) | 31.35 g |
| Volume of sour byproduct (malic acid and sugars) | @ 35 L |

Example 2 results:

MONTMORENCY cherry

| | |
|---|---|
| Weight of IQF cherries | 30.45 kg |
| Weight of dried pulp | 895 g |
| Volume of juice | 24.03 L |

| -continued | |
|---|---|
| Weight of anthocyanins, bioflavonoids and phenolics (red powder) | 47 g |
| Volume of cherry by-product (malic acid and sugars) | @ 75 L |

The red powders of Examples 1 and 2 were preferably mixed with dried pulp as a carrier and tableted into 1 to 1000 mg tablets including the carrier (1 adult daily dose).

Various food grade acids can be added to the isolated anthocyanins, bioflavonoids and phenolics to prevent decomposition. Preferably they do not add flavor. Ascorbic acid (vitamin C) is preferred. The acid can be added before or after the drying of the cherry compounds.

For small scale processing, lyophilization is used to remove water. For larger scale production, drying in an air circulating oven is preferred.

EXAMPLE 3

Figure 6:
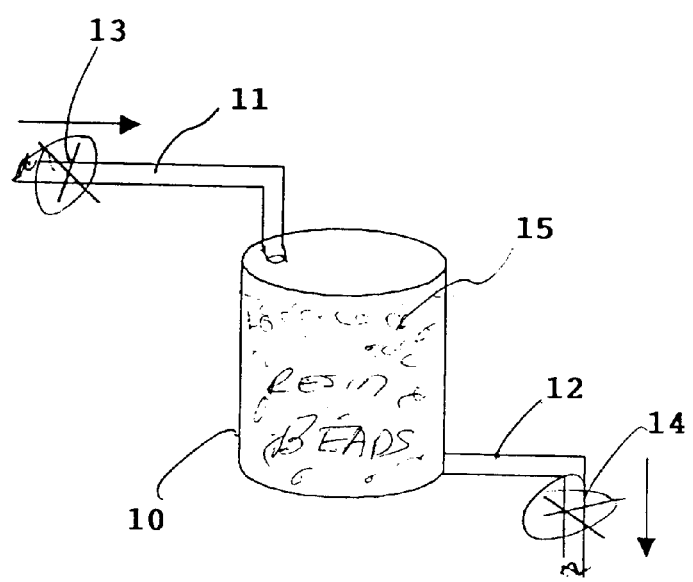
FIG. 6 is a schematic drawing showing the use of an open vessel 10 for holding resin beads, which remove anthocyanins and phenolics from the cherry juice.

As shown in FIG. 6, an open vessel 10 is provided with an inlet line 11 and an outlet line 12, with valves 13 and 14, respectively. The resin beads 15 are provided in the open vessel 10. Water is introduced into the vessel 10 and then removed through outlet line 12 and discarded. The cherry juice (without the pulp or pits) as in Example 1 is introduced to the vessel 10 and allowed to stand for 25 minutes. The temperature of the water and juice is between about 20 and 30° C. The cherry juice residue containing malic acid and sugars is then removed through the outlet line 12 and retained as a food flavoring. The resin 15 in the vessel is then washed again with water from inlet line 11 and then removed and discarded through outlet line 12. The anthocyanins, bioflavonoids and phenolics on the resin particles are then extracted using 95% ethanol introduced through inlet line 11. The ethanol containing the anthocyanins, bioflavonoids and phenolics is removed from the vessel 10. The ethanol is removed from the anthocyanins, bioflavonoids and phenolics and dried using flash drying under nitrogen. The resulting powder is preferably then mixed with dried cherry pulp or other carrier as in Example 1. The resin particles are washed with water and then the resins and ethanol are recycled many times.

EXAMPLE 4

Crude ethyl acetate extracts from cherries (containing anthocyanins, bioflavonoids and phenolics) were tested in aqueous solution under various conditions using a fluorescent assay for antioxidant activity. The fluorescent assay is described first.

Fluorescence assay for antioxidant activity (general): The need to screen large numbers of compounds or extracts for antioxidant activity requires that a model system (or systems) be employed which reasonably well represents the structural and functional characteristics of the composition alone or in the food product. The test must also be sensitive, rapid, and inexpensive. A fluorescence-based assay for evaluating antioxidant efficacy was used (Arora, A., and G. M. Strasburg, J. Am. Chem. Soc. 1996)). Large unilamellar vesicles consisting of 1-stearoyl-2-linoleoy-sn-glycero-3-phosphocholine were prepared, which closely resemble the properties of biological membranes, one of the primary sites of peroxidation. A fluorescent probe, 1,6-diphenylhexatriene propionic acid, is incorporated into the membranes such that the polar head group anchors the probe near the aqueous interface, while the hydrophobic portion lies parallel to the fatty acid chains. This probe reacts with the free radicals generated during peroxidation, resulting in a decrease in fluorescence intensity with time. A peroxidation initiator (such as ferrous metal ions or the free radical generator AAPH (Azobis-[2-amidino propane hydrochloride]) is used to start the reaction, and the kinetics of fluorescence decrease are determined in the presence or absence of the antioxidant composition to be tested. An assay for a compound at a given concentration presently takes only twenty-one minutes, consumes only a few micrograms of lipid, and can be readily conducted with a simple fluorometer.

Large unilamellar vesicles (LUVs) were prepared from 1-stearoyl-2-linoleoyl-sn-glycero-3-phosphocholine according to the procedure outlined by MacDonald et al (MacDonald, R. C., et al., Biochim. Biophys. Acta 1061:297–303 (1991)). Briefly, the lipid was dissolved in chloroform, and was dried to a thin film using a rotary evaporator. The dried film was resuspended in an aqueous buffer, and was repeatedly extruded through a polycarbonate filter of 100 nm pore size using a Liposofast piposome extruder (Avestin, Inc., Ottawa, Canada). The homogeneity of size (80–100 nm) and the unilamellar nature of the vesicles were confirmed using freeze-fracture scanning electron microscopy. The fluorescent probe, diphenylhexatriene-propionic acid (DPH-PA), was incorporated into the vesicles during preparation at a mole ratio of 1:350 (probe:lipid). For the fluorescence experiments, LUVs containing.DPH-PA is suspended at a final concentration of 100 $\mu$M in 100 mM NaCl, 50 mM tris-HEPES buffer at pH 7.0. The fluorescent probe was excited at 384 nm and emission was monitored at 423 nm. Lipid oxidation is inhibited in the LUVs by addition of ferrous ions or the free radical generator AAPH; the progress was monitored by the decrease of the fluorescence intensity of DPH-PA resulting from reaction with free radicals generated over twenty-one minutes. A plot of the decrease of fluorescence intensity as a function of time was used to determine the kinetics of lipid oxidation. The results show that a mixture of the crude anthocyanin extract with ethylacetate was effective in inhibiting oxidation.

Solvent extraction of the anthocyanins, bioflavonoids and phenolics can be used; however this is not preferred where the product is to be used as a food and for expense reasons. Where the preferred adsorbent resins are used, this step is unnecessary. It is also possible to separate and recombine the components using chromatography; however, for the purpose of the present invention, this is far too expensive since it involves high pressure liquid chromatography.

EXAMPLE 5

The compositions were tested for anti-inflammatory activity using cyclooxygenase I and II (COX-I and COX-II) in an assay as described in Wang et al., J. Nat. Products 62:294–296 (1999); Wang et al., J. of Ag. and Food Chemistry, 47: 840–844 (1999) and Wang et al., J. of Nat. Products, 62:86–88 (1999). The results were that the compositions exhibited anti-inflammatory activities, specifically strong inhibition of COX-I and COX-I.

EXAMPLES 6, 7 AND 8

Processing of Raspberries, Blueberries, and Blackberries:

Raspberries (339 g), Blueberries (350 g) and Blackberries (670 g) were defrosted and blended separately with 500 mL of water in an industrial Waring blender. The mixtures were centrifuged at 10,000 rpm for 20 minutes and juice was decanted. The residues (pulp) were further pressed with cheesecloth to remove any additional juice. The juice after centrifugation was about 775 mL (Raspberries), 700 mL (Blueberries), and 1100 mL (Blackberries).

The pulp was lyophilized at 15° C. The juices were processed on XAD-16 resin to separate anthocyanins and phenolics from sugars and acids. The XAD-16 resin (1 kg) was washed with ethanol (1–2 L) and then washed with water (6 L). The resin was allowed to stand in water for 1 hour before loading into a glass column (10×90 cm) with a cotton plug. The packed column was washed with water (2 L) before loading the juice for separation. 800 mL of juice was purified each time. The juice was added on to the surface of the column and allowed to settle with no flow. It was then eluted with water and the first 1 L was discarded. The next 2 L of washing was collected, since it contains the sugars and acids. The column was then washed with an additional 3 L of water for all juices. After removing sugars and acids, the column was eluted each time with ethanol (1.3 L, each for Raspberries and Blueberries and 1.0 L for Blackberries) and collected the red solution containing anthocyanins and phenolics (700 mL). The column was then run dry and washed with 10 L of water before repeating the process.

The red alcoholic solution was then evaporated under vacuum to remove ethanol and the aqueous solution, stabilized with 50 ppm ascorbic acid, was lyophilized at 10° C. The red powders were collected and stored at −20° C. The results are shown in Table 1.

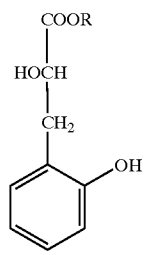

(2)

where R is selected from the group consisting of H and $CH_3$; and

| Fruit | weight (g) | Water added to make juice (mL) | Volume of juice after centrifugation (mL) | Volume of water needed to remove acids and sugars (mL) | Volume of EtOH used to elute Anthocyanins and phenolics (mL) | Weight of residues after lyophilization (g) | Weight of Anthocyanins and phenolics (g) |
|---|---|---|---|---|---|---|---|
| Raspberries | 339.0 | 500 | 775 | 6000 | 1300 | 13.76 | 0.6752 |
| Blueberries | 350.0 | 500 | 700 | 6000 | 1300 | 52.20 | 0.7110 |
| Blackberries | 670.0 | 500 | 1100 | 6000 | 2000 | 51.65 | 1.4420 |

It is intended that the foregoing description be only illustrative of the present invention and that the present invention be limited only by the hereinafter appended claims.

I claim:
1. A consumable composition with antioxidant and anti-inflammatory activity which comprises in admixture:
   (a) a dried mixture of isolated anthocyanins, bioflavonoids and phenolics from an edible berry free of acids and sugars of the berry and berry solids wherein the mixture of anthocyanins, bioflavonoids and phenolics are provided in an amount that is effective to provide antioxidant and anti-inflammatory activity and the mixture includes at least one phenolic selected from the group consisting of

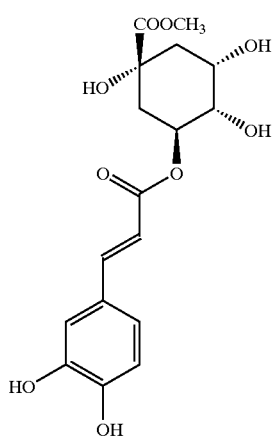

(1)

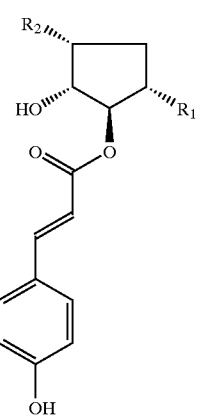

(3)

wherein $R_1$ is OH and $R_2$ is H or $R_1$ is H and $R_2$ is OH; and
   (b) a food grade carrier wherein the weight ratio of (a) to (b) is between about 0.1 to 100 and 100 to 0.1.
2. The composition of claim 1 wherein the carrier is a dried pulp of a cherry.
3. A method for providing antioxidant and anti-inflammatory activity to a mammal which comprises:
   feeding the mammal a consumable composition with the antioxidant and anti-inflammatory activity which comprises in admixture
   (a) a dried mixture of isolated anthocyanins, bioflavonoids and phenolics from an edible berry free of organic acids and sugars of the berry and berry solids, wherein the mixture includes at least one phenolic selected from the group consisting of (1)

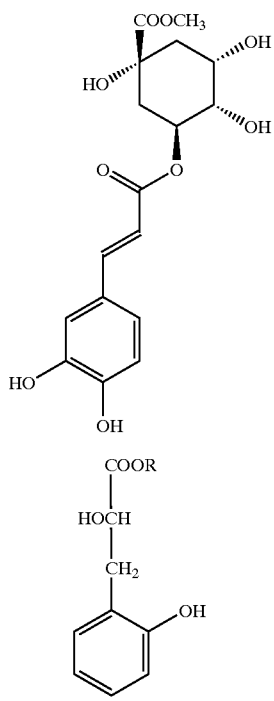

(2)

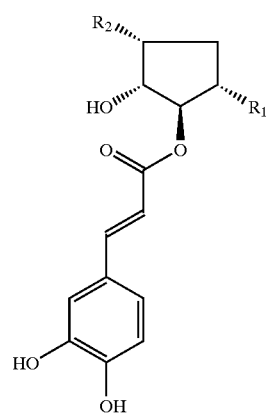

where R is selected from the group consisting of H and CH$_3$; and (3)

wherein R$_1$ is OH and R$_2$ is H or R$_1$ is H and R$_2$ is OH; and (b) a food grade carrier wherein the weight ratio of (a) to (b) is between about 0.1 to 100 and 100 to 0.1.

4. The method of claim 3 wherein the carrier is a dried pulp of a berry.

5. The method of claim 3 wherein the mammal is human.

6. The method of claim 3 wherein the dried mixture of isolated anthocyanins, bioflavonoids and phenolics is prepared by (a) providing an aqueous solution containing juice from the berry;

(b) removing the anthocyanins, bioflavonoids, and phenolics from the organic acids and sugars of the berry and the berry solids in the solution by adsorbing the anthocyanins, bioflavonoids, and phenolics onto a resin which does not adsorb the organic acids and sugars of the berry and the berry solids, wherein the resin is certified for use with food products;

(c) eluting the anthocyanins, bioflavonoids, and phenolics from the resin with an eluant to produce the mixture of the anthocyanins, bioflavonoids and phenolics in the eluant;

(d) separating the eluant from the mixture; and (e) drying the mixture.

7. The method of claim 3 wherein the dried mixture of isolated anthocyanins, bioflavonoids and phenolics is prepared by (a) providing a batch of the edible berries, wherein the berries are fresh or quick frozen and thawed;

(b) blending the berries and separating pulp from juice;

(c) extracting the anthocyanins, bioflavonoids and phenolics with the organic acids and sugars of the berry and the berry solids into an aqueous solution from the juice and pulp;

(d) removing the anthocyanins, bioflavonoids, and phenolics from the organic acids and sugars of the berry and berry solids in the solution by adsorbing the anthocyanins, bioflavonoids, and phenolics onto adsorbent resin particles which do not adsorb the organic acids and sugars of the berry and the berry solids, wherein the resin particles are certified for use with food products;

(e) washing the resin particles with a lower alkanol to remove the anthocyanins, bioflavonoids and phenolics as a mixture from the resin particles;

(f) separating the alkanol from the mixture;

(g) repeating steps (a) to (e) with the separated alkanol and the resin particles from which the mixture has been removed with multiple batches of the berries; and (h) drying the mixture.

8. The method of claim 7 wherein the alkanol is ethanol.

* * * * *

UNITED STATES PATENT AND TRADEMARK OFFICE
CERTIFICATE OF CORRECTION

PATENT NO. : 6,676,978 B1
DATED : January 13, 2004
INVENTOR(S) : Muraleedharan G. Nair It is certified that error appears in the above-identified patent and that said Letters Patent is hereby corrected as shown below:

Column 6,
Line 2, "3-(21-hydroxyphenyl)" should be -- 3-(2'-hydroxyphenyl) --.
Line 4, "ad β-sitosterol" should be -- and β-sitosterol --.

Column 8,
Line 52, "COX-I and COX-I" should be -- COX-I and COX-II --.

Signed and Sealed this

Fourth Day of May, 2004

JON W. DUDAS
*Acting Director of the United States Patent and Trademark Office*